US00PP31458P2

(12) United States Plant Patent
Nebelmeir

(10) Patent No.: US PP31,458 P2
(45) Date of Patent: Feb. 18, 2020

(54) POINSETTIA PLANT NAMED 'LAZZPONEO'

(50) Latin Name: ***Euphorbia pulcherrima* Willd.**
Varietal Denomination: LAZZPONEO

(71) Applicant: Johannes Nebelmeir, Munden (DE)

(72) Inventor: Johannes Nebelmeir, Munden (DE)

(73) Assignee: LAZZERI SOCIETA AGRICOLA a.r.i., Sabausia (IT)

( * ) Notice: Subject to any disclaimer, the term of this patent is extended or adjusted under 35 U.S.C. 154(b) by 0 days.

(21) Appl. No.: 16/350,928

(22) Filed: Feb. 1, 2019

(51) Int. Cl.
*A01H 5/02* (2018.01)
*A01H 6/38* (2018.01)

(52) U.S. Cl.
USPC ..... Plt./307
CPC ..... *A01H 6/38* (2018.05)

(58) Field of Classification Search
USPC ..... Plt./307
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of Poinsettia plant named 'LAZZPONEO', characterized by its compact, broadly upright and uniformly mounding plant habit; moderately vigorous growth habit; freely branching habit; dark green-colored leaves; large and full inflorescences with light red-colored flower bracts; and excellent post-production longevity.

2 Drawing Sheets

Botanical designation: *Euphorbia pulcherrima* Willd.
Cultivar denomination: 'LAZZPONEO'.

BACKGROUND OF THE INVENTION

The present invention relates to a new and distinct cultivar of Poinsettia plant, botanically known as *Euphorbia pulcherrima* Willd. and hereinafter referred to by the name 'LAZZPONEO'.

The new Poinsettia plant is a product of a planned breeding program conducted by the Inventor in Sabaudia, Italy. The objective of the breeding program is to create new compact and freely-branching Poinsettia plants with attractive flower bracts.

The new Poinsettia plant is a naturally-occurring branch mutation of *Euphorbia pulcherrima* Willd. 'Monreale Marble', not patented. The new Poinsettia plant was discovered and selected by the Inventor on a single flowering plant of 'Monreale Marble' in a controlled greenhouse environment in Sabaudia, Italy in December, 2015.

Asexual reproduction of the new Poinsettia plant by terminal vegetative cuttings in a controlled greenhouse environment in Sabaudia, Italy since May, 2016 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'LAZZ- PONEO'. These characteristics in combination distinguish 'LAZZPONEO' as a new and distinct Poinsettia plant:

1. Compact, broadly upright and uniformly mounding plant habit.
2. Moderately vigorous growth habit.
3. Freely branching habit.
4. Dark green-colored leaves.
5. Large and full inflorescences with light red-colored flower bracts.
6. Excellent post-production longevity.

Plants of the new Poinsettia can be compared to plants of the mutation parent, 'Monreale Marble'. Plants of the new Poinsettia differ primarily from plants of 'Monreale Marble' in flower bract color as plants of the new Poinsettia have light red-colored flower bracts whereas plants of 'Monreale Marble' have light red and white bi-colored flower bracts.

Plants of the new Poinsettia can be compared to plants of *Euphorbia pulcherrima* Willd. 'Fiscor Fire', disclosed in U.S. Plant Pat. No. 12,992. In side-by-side comparisons, plants of the new Poinsettia differ primarily from plants of 'Fiscor Fire' in the following characteristics:

1. Plants of the new Poinsettia are more freely branching than plants of 'Fiscor Fire'.
2. Leaves of plants of the new Poinsettia are darker green in color than leaves of plants of 'Fiscor Fire'.
3. Plants of the new Poinsettia flower seven to ten days later than plants of 'Fiscor Fire'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet comprises a side perspective view of a typical flowering plant of 'LAZZPONEO' grown in a container.

The photograph on the second sheet is a close-up view of a typical inflorescence of 'LAZZPONEO'.

DETAILED BOTANICAL DESCRIPTION

The aforementioned photographs and following observations and measurements describe plants grown during the autumn and winter in 13-cm containers in a glass-covered greenhouse in Merano, Italy and under cultural practices typical of commercial Poinsettia production. During the production of the plants, day temperatures ranged from 15° C. to 20° C., night temperatures ranged from 10° C. to 15° C. and light levels ranged from 40 to 55 klux. Plants were pinched one time two weeks after planting, grown under natural daylength conditions and were five months old when the photographs and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. '*LAZZPONEO*'.

Parentage: Naturally-occurring branch mutation of *Euphorbia pulcherrima* Willd. 'Monreale Marble', not patented.

Propagation:

*Type.*—Terminal vegetative cuttings.

*Time to initiate roots, summer.*—About two weeks at soil temperatures ranging from 22° C. to 25° C. and ambient temperatures ranging from 25° C. to 30° C.

*Time to produce a rooted young plant, summer.*—About 24 days at soil temperatures ranging from 22° C. to 25° C. and ambient temperatures ranging from 25° C. to 30° C.

*Root description.*—Medium to thin, slightly fleshy; typically pale creamy white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, broadly upright and uniformly mounded plant habit; inverted triangle with rounded crown; large and full inflorescences positioned above the foliar plane; moderately vigorous growth habit and moderate growth rate.

*Plant height, soil level to top of floral plane.*—About 27 cm.

*Plant diameter or spread.*—About 45 cm.

*Lateral branch description.*—Branching habit: Freely branching habit with about five to seven lateral branches developing after pinching. Length: About 20 cm. Diameter: About 8 mm. Internode length: About 8 mm to 12 mm. Strength: Strong. Texture and luster: Smooth, glabrous; semi-glossy. Color: Close to 146B.

*Leaf description.*—Arrangement: Alternate, simple. Length: About 12 cm to 15 cm. Width: About 7 cm to 10 cm. Shape: Ovate. Apex: Acuminate. Base: Cuneate. Margin: One to three shallow lobes; slightly undulate. Venation pattern: Pinnate, reticulate. Texture and luster, upper and lower surfaces: Smooth, glabrous; matte. Color: Developing leaves, upper surface: Close to 139A to 139B. Developing leaves, lower surface: Close to 137B to 137C. Fully expanded leaves, upper surface: Close to 139A; venation, close to 146A. Fully expanded leaves, lower surface: Close to 137B; venation, close to 146C. Petioles: Length: About 4 cm to 6 cm. Diameter: About 2.5 mm to 3 mm. Strength: Moderately strong. Texture and luster, upper and lower surfaces: Smooth, glabrous; semi-glossy. Color, upper surface: Close to 184A. Color, lower surface: Close to 184C.

Inflorescence description:

*Inflorescence type and habit.*—Large full inflorescences are compound corymbs of cyathia with colored flower bracts subtending the cyathia; one inflorescence per lateral branch with inflorescences positioned above and beyond the foliar plane.

*Fragrance.*—None detected.

*Natural flowering season.*—Plants flower naturally during the late autumn to winter under long nyctoperiod conditions; inflorescence initiation and development can be induced under artificial long nyctoperiod conditions; response time is about 8 to 8.5 weeks.

*Post-production longevity.*—Excellent post-production longevity; plants of the new Poinsettia maintain good substance and bract color for about four to six weeks; flower bracts persistent.

*Inflorescence width.*—About 20 cm to 25 cm.

*Inflorescence height.*—About 4 cm to 6 cm.

*Flower bracts.*—Quantity per inflorescence: About 15. Length: About 10.5 cm to 12.5 cm. Width: About 6 cm to 9 cm. Shape: Ovate. Apex: Acuminate. Base: Cuneate. Margin: Entire or occasionally shallowly lobed; slightly undulate. Aspect: Horizontal to slightly drooping. Venation: Pinnate. Texture and luster, upper and lower surfaces: Moderately rugose, glabrous; matte. Color: Developing bracts, upper surface: Close to 44A. Developing bracts, lower surface: Close to 45B. Fully expanded bracts, upper surface: Close to 42A; venation, close to 42A; color becoming closer to 45A with development. Fully expanded bracts, lower surface: Close to 43B; venation, close to 43B; color becoming closer to 45C with development. Bract petioles: Length: About 2.2 cm. Diameter: About 2 mm. Texture and luster, upper and lower surfaces: Smooth, glabrous; semi-glossy. Color, upper surface: Close to 46A. Color, lower surface: Close to 46C.

*Cyathia.*—Quantity per corymb: About six to eight. Length: About 6 mm. Width: About 5 mm. Shape: Cylindrical to ovoid. Texture and luster, inner and outer surfaces: Smooth, glabrous; matte. Color, developing, inner and outer surfaces: Close to 144A. Color, fully developed, inner surface: Close to 145A. Color, fully developed, outer surface: Close to 145B. Nectaries: Quantity per cyathium: Typically one. Length: About 4 mm. Diameter: About 2 mm. Shape: Lip-shaped. Texture and luster, inner and outer surfaces: Smooth, glabrous; matte. Color, fully developed, inner surface: Close to 14A. Color, fully developed, outer surface: Close to 13A.

*Pedicels.*—Length: About 3 mm to 5 mm. Diameter: About 1 mm. Strength: Moderately strong. Texture and luster: Smooth, glabrous; semi-glossy. Color: Close to 145B.

*Reproductive organs.*—Stamens: To date, stamen development has not been observed on plants of the new Poinsettia. Pistils: Quantity per cyathia: Typically, one or two. Pistil length: About 3 mm to 4 mm. Style length: About 3 mm to 4 mm. Style shape: Recurved. Fruits: Quantity: None to very few with one to three seeds. Length: About 8 mm to 12 mm. Diameter: About 6 mm to 10 mm. Texture: Smooth, glabrous.

Pathogen & pest resistance: To date, plants of the new Poinsettia have not been shown to be resistant to pathogens and pests common to Poinsettia plants.

It is claimed:

1. A new and distinct Poinsettia plant named 'LAZZPONEO' as illustrated and described.

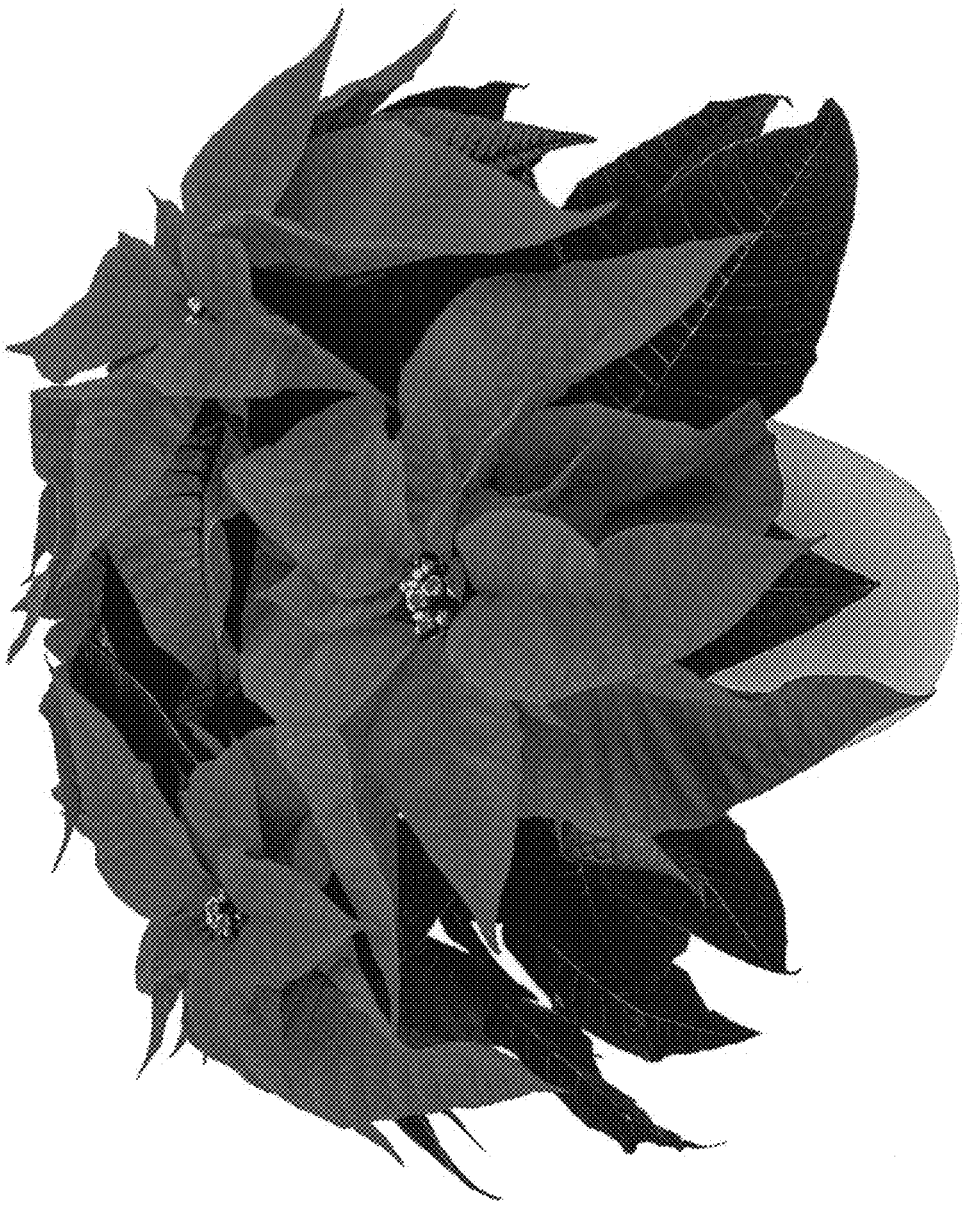

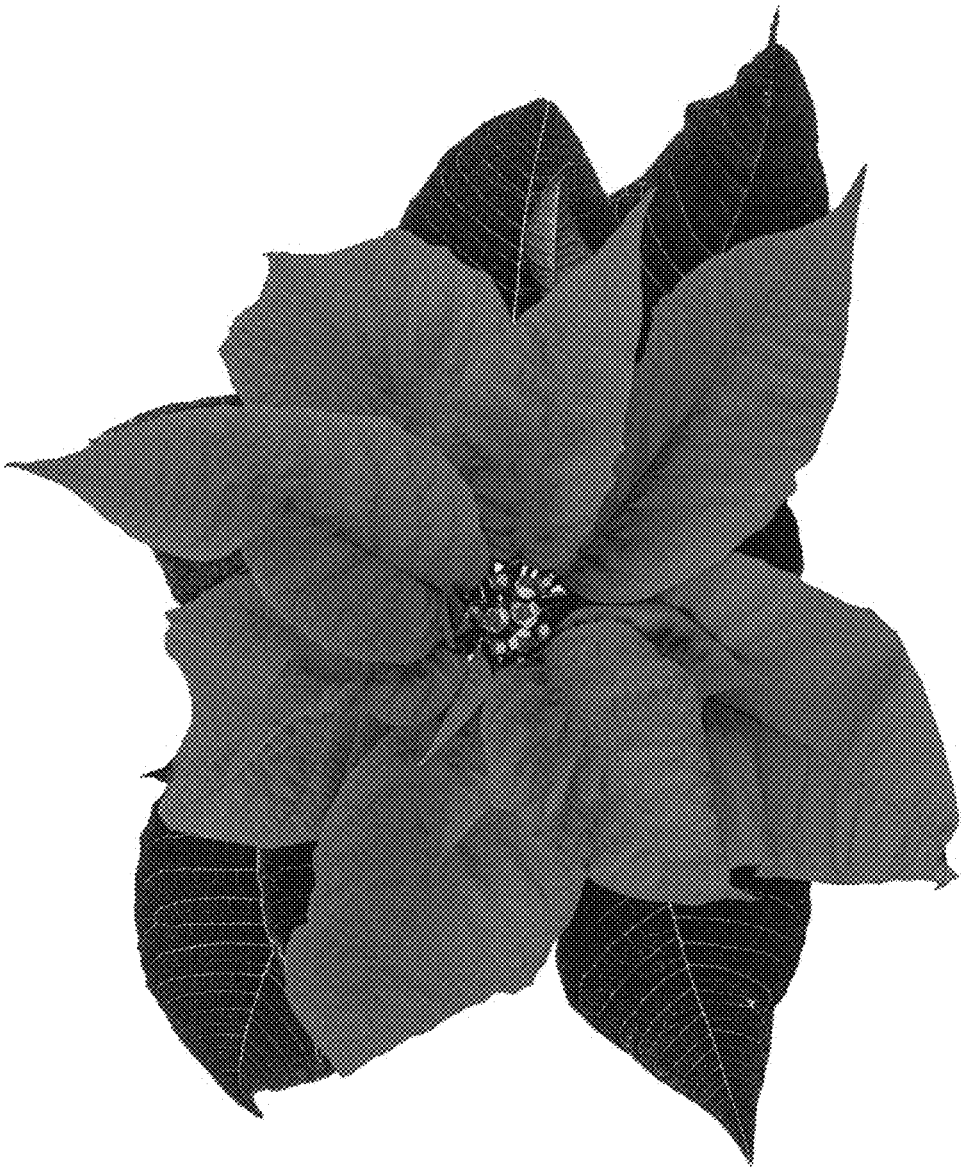

* * * * *